(12) United States Patent
Savoy et al.

(10) Patent No.: US 8,450,131 B2
(45) Date of Patent: May 28, 2013

(54) IMPRINTED SEMICONDUCTOR MULTIPLEX DETECTION ARRAY

(75) Inventors: Steve M. Savoy, Austin, TX (US);
Jeremy J. John, Austin, TX (US);
Daniel R. Mitchell, Austin, TX (US);
Michael K. McAleer, Austin, TX (US)

(73) Assignee: Nanohmics, Inc., Austin, TX (US)

( * ) Notice: Subject to any disclaimer, the term of this patent is extended or adjusted under 35 U.S.C. 154(b) by 0 days.

(21) Appl. No.: 13/004,381

(22) Filed: Jan. 11, 2011

(65) Prior Publication Data

US 2012/0178199 A1 Jul. 12, 2012

(51) Int. Cl.
*G01N 27/414* (2006.01)
*H01L 27/088* (2006.01)
*H01L 21/203* (2006.01)
*H01L 29/06* (2006.01)

(52) U.S. Cl.
CPC .......... *G01N 27/4148* (2013.01); *H01L 27/088* (2013.01); *H01L 29/0673* (2013.01)
USPC .............................. 438/49; 438/503; 438/508

(58) Field of Classification Search
USPC .... 438/49, 82, 99, 706, 57, 74, 478; 430/369, 430/315, 322, 324; 977/762, 887
See application file for complete search history.

(56) References Cited

U.S. PATENT DOCUMENTS

| | | |
|---|---|---|
| 5,309,085 A | 5/1994 | Sohn |
| 6,334,960 B1 | 1/2002 | Willson et al. |
| 6,426,184 B1 | 7/2002 | Gao et al. |
| 6,914,279 B2 | 7/2005 | Lu et al. |
| 6,965,040 B1 | 11/2005 | Gao et al. |
| 7,235,389 B2 | 6/2007 | Lim et al. |
| 7,253,434 B2 | 8/2007 | Golovchenko et al. |
| 7,256,435 B1 | 8/2007 | Kornilovich et al. |
| 7,301,199 B2 | 11/2007 | Lieber et al. |
| 7,335,526 B2 | 2/2008 | Peters et al. |
| 7,410,904 B2 | 8/2008 | Stasiak et al. |
| 2002/0006632 A1 | 1/2002 | Ponnampalam et al. |
| 2003/0102510 A1 | 6/2003 | Lim et al. |
| 2004/0238379 A1 | 12/2004 | Lindsay et al. |
| 2004/0256685 A1 | 12/2004 | Chou et al. |
| 2005/0089924 A1 | 4/2005 | Ho et al. |

(Continued)

OTHER PUBLICATIONS

Hahm, Jong-in; Lieber, Charles; "Direct Ultrasensitive Electrical Detection of DNA and DNA sequence variations using Nanowire Nanosensors", Nano Letters, vol. 4, No. 1, pp. 51-54, 2004.

(Continued)

*Primary Examiner* — Olik Chaudhuri
*Assistant Examiner* — Wilner Jean Baptiste
(74) *Attorney, Agent, or Firm* — Claude E. Cooke, Jr.; Cooke Law Firm

(57) ABSTRACT

An array of sensor devices, each sensor including a set of semiconducting nanotraces having a width less than about 100 nm is provided. Method for fabricating the arrays is disclosed, providing a top-down approach for large arrays with multiple copies of the detection device in a single processing step. Nanodimensional sensing elements with precise dimensions and spacing to avoid the influence of electrodes are provided. The arrays may be used for multiplex detection of chemical and biomolecular species. The regular arrays may be combined with parallel synthesis of anchor probe libraries to provide a multiplex diagnostic device. Applications for gas phase sensing, chemical sensing and solution phase biomolecular sensing are disclosed.

17 Claims, 8 Drawing Sheets

U.S. PATENT DOCUMENTS

| | | | |
|---|---|---|---|
| 2005/0116263 | A1 | 6/2005 | Lu et al. |
| 2005/0224346 | A1 | 10/2005 | Holm-Kennedy |
| 2005/0272059 | A1 | 12/2005 | Gao et al. |
| 2006/0054941 | A1 | 3/2006 | Lu et al. |
| 2006/0060924 | A1 | 3/2006 | Ogawa et al. |
| 2006/0141474 | A1 | 6/2006 | Miyahara et al. |
| 2006/0147983 | A1 | 7/2006 | O'uchi |
| 2006/0205013 | A1 | 9/2006 | Shim et al. |
| 2007/0031961 | A1 | 2/2007 | Ho et al. |
| 2010/0084376 | A1* | 4/2010 | Khusnatdinov et al. ........ 216/39 |
| 2010/0136739 | A1* | 6/2010 | Li et al. ............................ 438/99 |
| 2010/0276665 | A1* | 11/2010 | Wang .............................. 257/15 |
| 2011/0254142 | A1* | 10/2011 | Wang et al. ................... 257/642 |

OTHER PUBLICATIONS

Resnick, D., "Step and Flash Imprint Lithography", Solid State Technology, Feb. 2007.

Gao, X. et al, "Light Directed Massively Parallel on-chip Synthesis of Peptide Arrays with t-Boc Chemistry", Proteomics, 2003.

Cui, Yi; Wei, Qingqiao; Park, Hongkun; Lieber, Charles; "Nanowire Nanosensors for Highly Sensitive and Selective Detection of Biological and Chemical Species", Science Magazine, vol. 293, p. 1289-1292, Aug. 17, 2001.

Kong, J., et al, "Nanotube molecular wires as chemical sensors", Science, 2000, vol. 287, p. 622.

Pan, Z.; Z. Dai; Z. Wang, "Nanobelts of semiconducting oxides", Science, 2001, vol. 291, p. 1947.

Comini, E et al, "Stable and highly sensitive gas sensors based on semiconducting oxide nanobelts," Applied Physics Letters, 2002, vol. 81 (10), p. 1869.

Colburn, M. et al.; Development and advantages of step-and-flash lithography, Solid State Technology, Jul. 2001, p. 67.

Remacle, F., et al., "Gating the conductivity of arrays of metallic quantum dots," Journal of Physical Chemistry B, 2003, 107, p. 13892.

Li, C. et al., "In2O3 nanowires as chemical sensors," Applied Physics Letters, 2003, 82(10), p. 1613.

Zhang, Y., et al., "Control of catalytic reactions at the surface of a metal oxide nanowire by manipulating electron density inside it," Nano Letters, 2004, 4(3), p. 403.

Fan, Z. et al., "ZnO nanowire field-effect transistor and oxygen sensing property," Applied Physics Letters, 2004, 85 (24), p. 5923.

Patolsky, F. et al., "Electrical detection of single viruses," Proceedings of the National Academy of Sciences, 2004, 101(39), p. 14017.

Wang, W. et al., "Label-free detection of small-molecule-protein interactions by using nanowire nanosensors," Proceedings of the National Academy of Sciences, 2005, 102(9), p. 3208.

Talapin, D., Murry, C., "PbSe nanocrystal solids for n- and p-channel thin film field-effect transistors," Science, 2005, 310, p. 86.

Wang, H., et al., "Hydrogen-selective sensing at room temperature with ZnO nanorods," Applied Physics Letters, 2005, 86, p. 243503.

Watanabe, A., Hojo, F., Miwa, T., "Field effect transistor based on organosoluble germanium nanoclusters," Applied Organometallic Chemistry, 2005, 19, p. 530.

Purushothaman, S.; Toumazou, C,; Ou, C.; "Protons and single nucleotide polymorphism detection: a simple use for the ion sensitive field effect transistor," Sensors and Actuators B, 2006, 114, p. 964.

Cheng, Y., et al., "Intrinsic characteristics of semi conducting oxide nanobelt field-effect transistors," Applied Physics Letters, 2006, 89, p. 093114.

Ingebrandt, S., et al., "Label-free detection of single nucleotide polymorphisms utilizing the differetial transfer function of field-effect transistors," Biosensors & Bioelectronics, 2007, 22, p. 2834.

Zhang, Q., Subramanian, V., "DNA hybridization detection with organic thin film transistors: Toward fast and disposable DNA microarray chips," Biosensors & Bioelectronics, 2007, 22, p. 3182.

Pourmand, N., et al., "Direct electrical detection of DNA synthesis," Proceedings of the National Academy of Sciences, 2006, 103(17), p. 6466.

Star, A. et al., "Label-free dectino of DNA hybridization using carbon nanotube netword field-effect transistors," Proceedings of the National Academy of Sciences, 2006, 103(4), p. 921.

Wang, D., Dai, H., "Germanium nanowires: form synthesis, surface chemistry, and assembly to devices," Applied Physics A, 2006, 85, p. 217.

* cited by examiner

FIG. 1 INSET

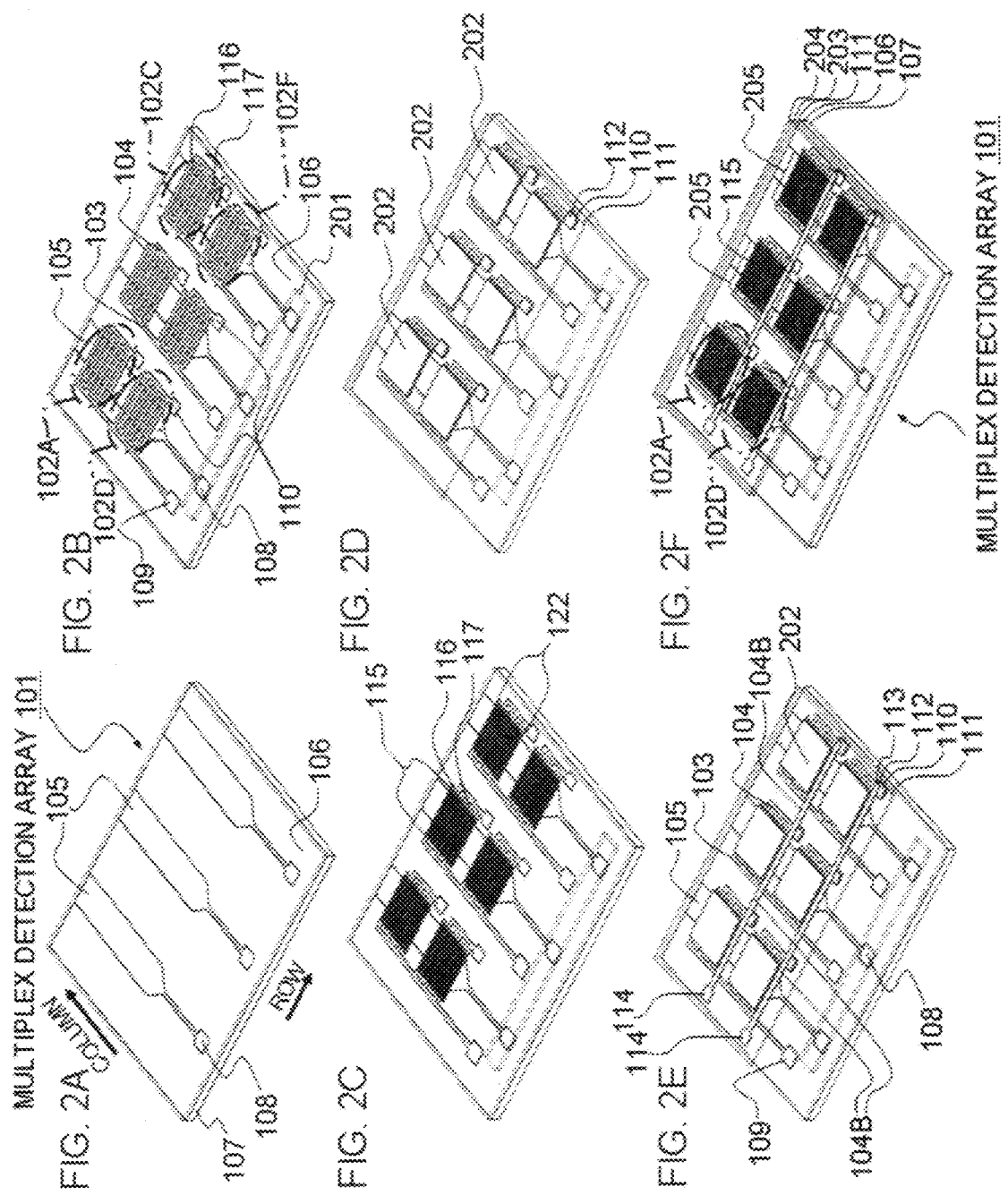

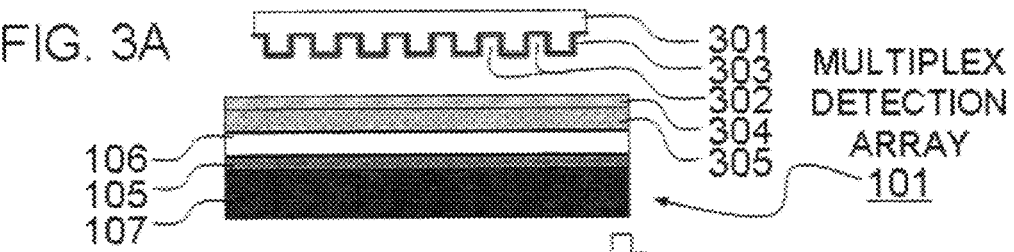
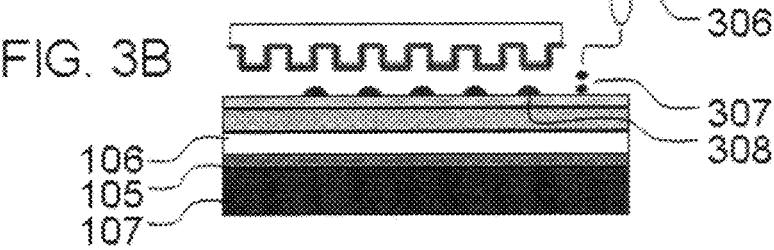
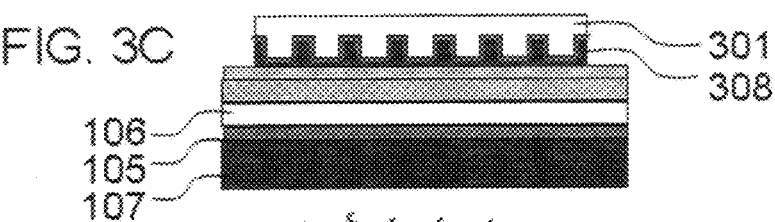
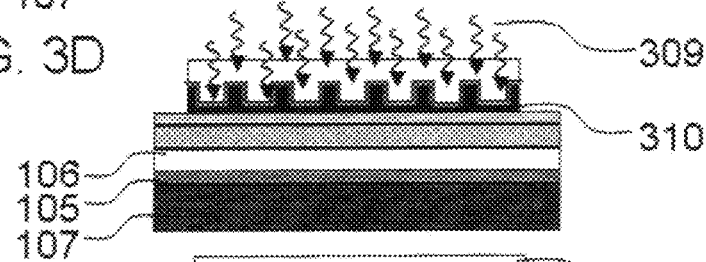
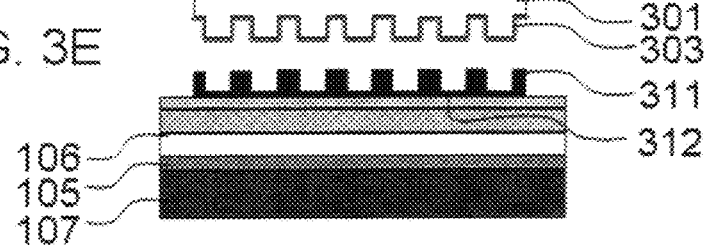

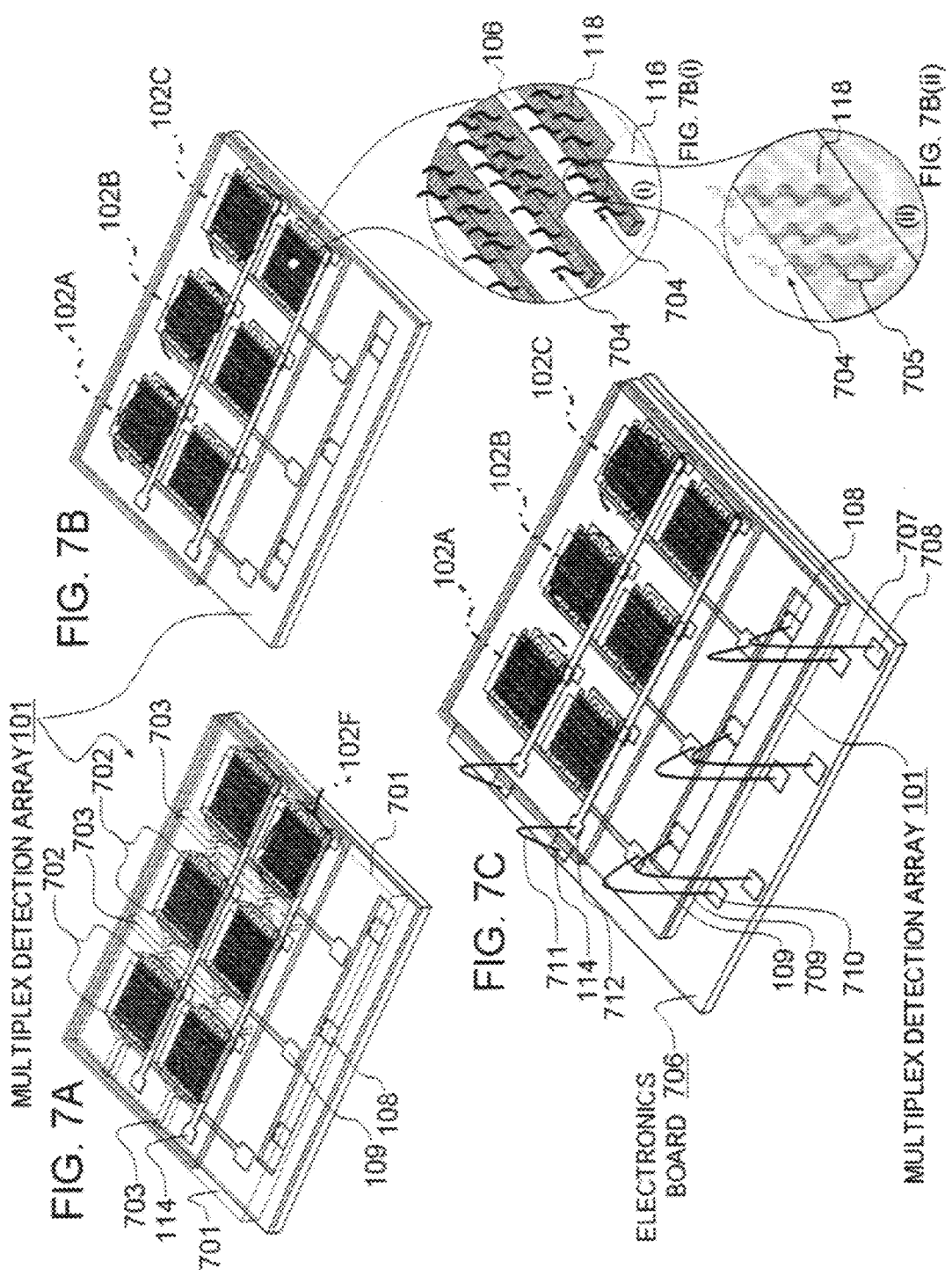

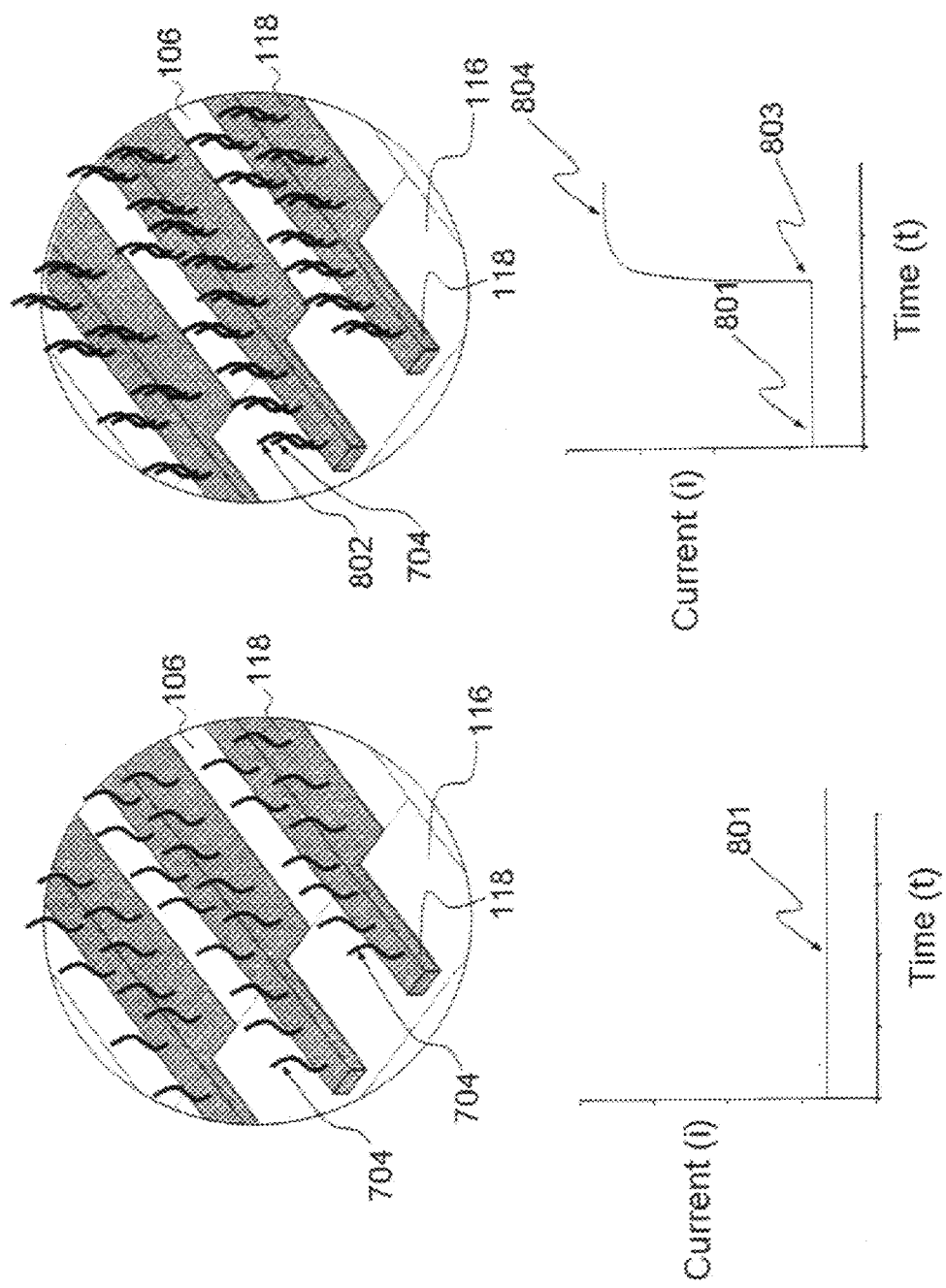

IMPRINTED SEMICONDUCTOR MULTIPLEX DETECTION ARRAY

BACKGROUND OF THE INVENTION

1. Field of the Invention

The present invention relates generally to active solid state devices, specifically to apparatus and method for making and using sensors with nanodimensional features that are responsive to molecular compounds, organisms or gas molecules.

2. Description of Related Art

The use of nanowires and nanotubes for label-free direct real-time detection of biomolecule binding is known in the art. Nanowires and nanotubes have the potential for very high-sensitivity detection since the depletion or accumulation of charge carriers, which is caused by binding of a charged biological macromolecules at the surface, can affect the entire cross-sectional conduction pathway of these nanostructures. See, e.g., Direct Ultrasensitive Electrical Detection of DNA and DNA Sequence Variations Using Nanowire Nanosensors, by Jong-in Hahm and Charles M. Lieber, *Nano Letters*, 2004 (Vol. 4, No. 1 pp. 51-54), which is incorporated by reference (hereinafter Lieber). Lieber discloses measurable conductance changes associated with hybridization of a Peptide Nucleic Acid (PNA) receptor with complimentary Deoxyribose Nucleic Acid (DNA) target molecule. A practitioner skilled in the art will appreciate that a Peptide Nucleic Acid (PNA) receptor could be substituted with a Deoxyribose Nucleic Acid (DNA) receptor or a Ribose Nucleic Acid (RNA) receptor.

U.S. Pat. No. 7,301,199 discloses nanowires fabricated using laser catalytic growth (LCG), and is incorporated by reference in its entirety. In LCG, a nanoparticle catalyst is used during the growth of the nanoscale wire. Laser vaporization of a composite target composed of a desired material and a catalytic material creates a hot, dense vapor. The vapor condenses into liquid nanoclusters through collision with a buffer gas. Growth begins when the liquid nanoclusters become supersaturated with the desired phase and can continue as long as reactant is available. Growth terminates when the nanoscale wire passes out of the hot reaction zone or when the temperature is decreased. In LCG, vapor phase semiconductor reactants required for nanoscale wire growth may be produced by laser ablation of solid targets, vapor-phase molecular species, or the like. To create a single junction within a nanoscale wire, the addition of the first reactant may be stopped during growth, and then a second reactant may be introduced for the remainder of the synthesis. Repeated modulation of the reactants during growth is also contemplated, which may produce nanoscale wire superlattices. LCG also may require a nanocluster catalyst suitable for growth of the different superlattice components; for example, a gold nanocluster catalyst can be used in a wide-range of III-V and IV materials. Nearly monodisperse metal nanoclusters may be used to control the diameter, and, through growth time, the length of various semiconductor nanoscale wires. This method of fabricating nanowires is known in the art, and constitutes one method of creating nano-scale features.

The use of photolithography for fabrication of micron-scale features is well known in the art. In "standard" photolithography, multiple steps are performed to pattern features on a surface. In the initial step, the surface, which may be a p- or n-doped silicon wafer, is cleaned of surface contaminants. Persons skilled in the art will appreciate that many planar surfaces can be patterned in this way, including surfaces with multiple layers, such as a substrate of p- or n-doped silicon, a middle layer of insulating silicon dioxide ($SiO_2$), with a top layer of metal. Next, adhesion promoters are added to the surface to assist in photoresist coating. Photoresist may be spin-coated onto the surface, forming a uniform thickness. The wafer containing the photoresist layer is then exposed to heat to drive off solvent present from the coating process. Next, a photomask, which may be made of glass with a chromium coating, is prepared. The features desired on the surface of the wafer are patterned on the photomask. The photomask is then carefully aligned with the wafer. The photomask is exposed to light, the transparent areas of the photomask allow light to transfer to the photoresist, the photoresist reacts to the light, and a latent image is created in the photoresist. The photoresist may be either positive or negative tone photoresist. If it is negative tone photoresist, it is photopolymerized where exposed and rendered insoluble to the developer solution. If it is positive tone photoresist, exposure decomposes a development inhibitor and developer solution only dissolves photoresist in the exposed areas. Simple organic solvents are sufficient to remove undeveloped photoresist. The techniques of "etch-back" and "lift-off" patterning are used at this stage. If the "etch-back" technique is used, the photoresist is deposited over the layer to be pattered, the photoresist is patterned, and the unpatterned areas of the layer are removed by etching. If the "lift-off" technique is used, photoresist is deposited followed by deposition of a thin film of desired material. After exposure, undeveloped photoresist is removed by the developer solvent and carries away the material above it into solution leaving behind the patterned features of the thin film on the surface. Removal of the remaining photoresist may be accomplished through oxygen plasma etching, sometimes called "ashing", or by wet chemical means using a "piranha" (3:1 $H_2SO_4$:$H_2O_2$) solution.

Although widely used and extremely useful as a micron-scale patterning tool, "standard" photolithography is limited in the resolution of the features it can pattern. The ability to project a clear image of a small feature onto the wafer is limited by the wavelength of the light that is used, and the ability of the reduction lens system to capture enough diffraction orders from the illuminated mask. The minimum feature size that a projection system can print is given approximately by: $CD = k_1 * (\lambda/NA)$; where CD is the minimum feature size (also called the critical dimension, target design rule); $k_1$ (commonly called $k_1$ factor) is a coefficient that encapsulates process-related factors, and typically equals 0.4 for production; $\lambda$ is the wavelength of light used; and NA is the numerical aperture of the lens as seen from the wafer. According to this equation, minimum feature sizes can be decreased by decreasing the wavelength, and increasing the numerical aperture, i.e. making lenses larger and bringing them closer to the wafer. However, this design method runs into a competing constraint. In modern systems, the depth of focus ($D_F$) is also a concern: $D_F = k_2 * (\lambda/(NA)^2)$. Here, $k_2$ is another process-related coefficient. The depth of focus restricts the thickness of the photoresist and the depth of the topography on the wafer. One solution known in the art is utilization of light sources with shorter wavelengths ($\lambda$), and creation of lenses with higher numeric apertures (NA). The drawback to this solution is the increasingly prohibitive high cost of fabricating complex sources and optics.

Nanoimprint Lithography (NIL) solves the problem of limited minimum feature sizes and high cost by patterning nanoscale features into a quartz plate, referred to as the "template" that can be applied directly to the surface of a wafer and transferring the pattern 1:1 into a photoresist layer. "Step and Flash Imprint Lithography," by Resnick, D., et al., *Solid State Technology*, (2007), Feb., 39, which is incorporated in its entirety by reference, discloses the method to pattern nanoscale features by first imprinting the features into a photoresist layer and dry etching the imprint layer into the desired thin film layer on a wafer. The S-FIL process, now generally known in the art as Nanoimprint Lithography (NIL), requires that electron beam lithography be first used to "write" the desired imprint pattern into the template. The template may be a quartz plate substrate coated with a chromium (Cr) layer. The electron beam resist is patterned and the pattern is transferred into the Cr layer and the final three-dimensional relief structure is etched into the quartz plate or "template." After transfer of the pattern into the quartz layer, the Cr layer is stripped, leaving an optically transparent template with the imprint pattern etched onto one surface.

To create the imprint pattern into a thin film layer on a wafer substrate, a low-viscosity photocurable monomer—known as the etch barrier—is dispensed on its surface. The transparent template is brought into contact with the monomer at a slight angle, creating a monomer wavefront that spreads across the surface and fills the three dimensional relief structures of the transparent template. UV light photopolymerizes the monomer and the template is separated from the wafer, leaving a solid replica of the reverse of the template on the substrate surface. Post-processing consists of a breakthrough etch of the residual layer of the monomer, followed by a selective etch into an organic layer and finally transfer of the pattern into the desired layer; for example a semiconductor thin film. Imprint lithography has been used to create feature CDs on the order of 20 nm in high density over large areas, e.g. 4-6" wafers during a single imprint process.

In a similar fashion, the reverse process (S-FIL/R) can be accomplished. This is achieved by imprinting the surface using the template followed by spinning on an organic layer. The organic layer is etched back to expose the top surface of the silicon-containing imprint which is then selectively etched to the substrate using the organic layer as an etch stop. A final set of etching conditions is used to transfer the pattern into the substrate material. Nanoimprint Lithography has the advantage of being limited only by physical resolution of the template rather than being limited by wavelength and numeric aperture, as in standard photolithography. As new methods emerge for template fabrication, a corresponding increase in feature resolution can be expected.

U.S. Pat. No. 6,426,184 discloses a method for massively parallel synthesis of DNA, RNA, and PNA molecules utilizing photogenerated reagents (PGR), and is incorporated herein by reference. The method involves a microfluidic chamber comprising a series of wells that act as reaction sites with a transparent sealed cover. Within each well, a "linker" molecule functionalized with a "reactive group" is attached to the substrate. The reactive group couples a "spacer group" which then couples the first nucleotide to the surface. The nucleotide bears a "protection group" initial. The reactive precursor to the PGR is introduced through the microfluidic chamber into the well sites. Selective wells receive light using a spatial light modulating device during a given exposure step which results in a "photogenerated reagent" within each well that was exposed. PGR is activated only in the wells that are exposed to light, thereby causing a chemical reaction with the protection group, and "de-protecting" the terminal nucleotide in the nucleic acid sequence. The PGR is flushed from the system, and a select nucleotide with a "protection group" is introduced. The nucleotide with "protection group" is covalently bonded to the end of the nucleic acid sequence in the selected wells. In all other wells that do not get exposed to light, no reaction takes place and no nucleotide coupling occurs during that exposure cycle. After proper washing, oxidation, and capping steps, the addition of the cycle is repeated in such a fashion to synthesize any combination of nucleotides onto surface-anchored nucleic acid sequences that are specific to each well. The process is continued until the oligonucleotides of interest are constructed over the entire array. The chemistry of building oligonucleotides is well known in the art. Because the sequence is known for each well in the multiplex detection array, diagnostic tests that result in a signal transduction event can be performed by first identifying if a reaction occurs for a given well, and second by determining the position, and hence identity of the "known" anchor probe sequence.

"Light Directed Massively Parallel On-chip Synthesis of Peptide Arrays with t-Boc Chemistry," by Gao, X., et al., *Proteomics*, (2003), 3, 2135 discloses PNA synthesis using t-Boc chemistry, and is incorporated by reference herein. This article is an example of chemical syntheses of anchor probe libraries known in the art.

What is needed is a cost-effective, time-efficient, reproducible method for fabricating arrays of nano-scale features on a single wafer to form a sensor device or a matrix of devices for multiplex detection of selected analytes using many simultaneous detection zones, by detecting changes in electrical characteristics of the nano-scale materials for each device. Method for making such sensors and arrays is needed.

SUMMARY OF INVENTION

The problem of reproducibly fabricating semiconducting active layers that provide the necessary nano-dimensional features for direct electrical detection in sensing applications is solved using nanoimprint lithography to define groups of semiconducting nanotraces between electrodes. Such groups may be used as a sensor or, when anchored probe molecules are covalently coupled or synthesized to the surfaces, be used for multiplex detection of analytes. Nanoimprint lithography also provides a method to fabricate arrays of semiconducting electrode "nanotraces" in a controllable and regular pattern in a single processing step. A method that provides controlled fabrication of nanophase features provides a means for detection of gases adsorbed on the semiconductor surfaces or multiplex detection of many simultaneous detection zones. Binding of complementary targets to the anchored probe molecules in the vicinity of the semiconducting active layer produces a change in electrical conductivity of the semiconducting active layer that can be monitored externally for each sensor device in the array in parallel.

BRIEF DESCRIPTION OF THE DRAWINGS

FIGS. 2 A-F illustrates the fabrication sequence for preparing the electrical base including the semiconductor nanotraces for the multiplex detection array.

FIGS. 3 A-E illustrate the process of preparing the imprint pattern for the semiconductor nanotraces.

FIGS. 7 A-C show the multiplex detection device preparation steps for performing PGR in the preferred embodiment and packaging onto the electronics board.

FIGS. 8 A-B show examples of the response generated during binding reactivity in the preferred embodiment.

DETAILED DESCRIPTION

Figure 1:
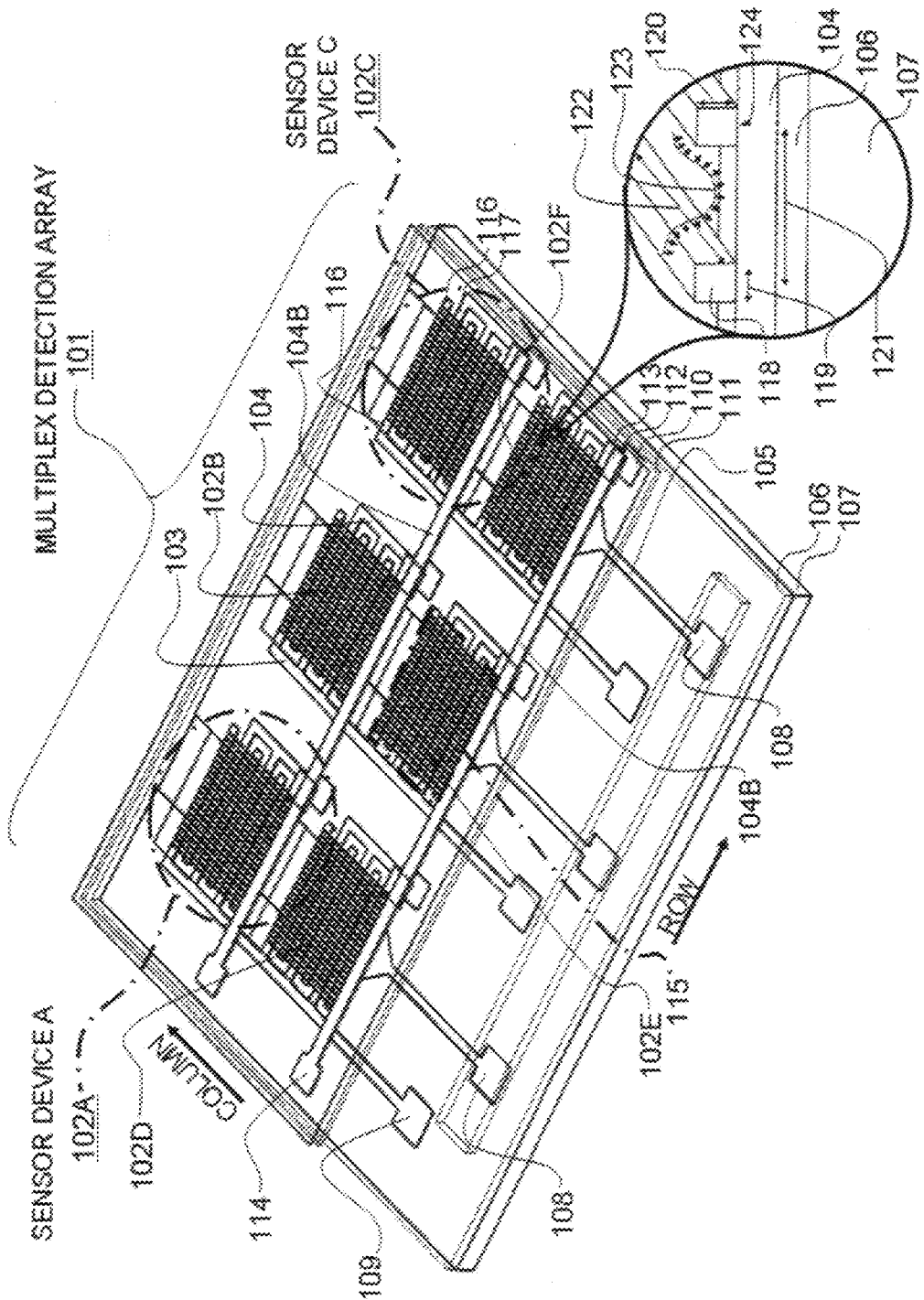
FIG. 1 depicts a subset of the multiplex detection array showing six sensor devices with the imprinted semiconductor nanotraces. The inset shows the features of an individual semiconductor nanotrace in the set of nanotraces disposed between the electrodes.

FIG. 1 illustrates an overview of a subset of the electrical detection portion of multiplex detection array 101, which consists of six individual sensor devices 102A-F. A single sensor device, e.g. 102A, is defined as a region that is independently electrically addressable from neighboring devices 102B-F in FIG. 1. Some of the features have been removed in this overview to enable a visual representation of the core components of multiplex detection array 101. Each sensor device 102 consists of a set of two interdigitated electrodes including source electrode 103, and drain electrode 104 of an individual sensor, e.g. sensor device 102B. A third gate electrode 105 may be positioned to cross under the interdigitated portion of each column of sensor devices 102, e.g. sensor devices 102C and 102F in FIG. 1. Gate electrode 105 is in a lower plane than source 103 and drain 104 electrodes and is separated by thin oxide dielectric layer 106 supported by a suitable substrate wafer 107, for example a silicon wafer or polymeric film. All of the electrodes 103-5 have relatively large scale features (~1-5 μm) that are patterned using standard lithography. In this example, gate electrode 105 is common to each column of sensor devices 102 and terminates at gate electrode bonding pad 108 in an area remote from the sensor devices 102. Similarly, source electrode 103 is common to all sensor devices 102 in each column in the array and terminates at source electrode bonding pad 109 in an area remote from sensor devices 102 and parallel with gate electrode 105. Each of the drain electrodes 104 terminates at each sensor device 102 at drain electrode stub bonding pad 110. A secondary process enables electrical continuity of drain electrode stub bonding pad 110 to be transferred to a higher plane that is separated by oxide insulating layer 111. Electrical continuity is transferred by metal filling of drain electrode vias 112 that are positioned over each drain electrode stub bonding pad 110 and below each drain electrode pick-up pad 113, which is in the higher plane. The portion of drain electrode 104B in this plane is common for each row of sensor devices 102; for example, sensor devices 102A-C and sensor devices 102D-F in FIG. 1, and terminates at drain electrode bonding pad 114. Drain electrodes 104B are perpendicular to the source 103 and gate 105 electrodes but in a different electrode plane to prevent shorting across the sensor devices 102.

In the center of each sensor device 102 is a set of parallel semiconductor "nanotraces" 115 that are perpendicular to and disposed across, the interdigitated finger region of the source 116 and drain 117 electrodes. Semiconductor nanotraces 115 can be fabricated using nanoimprint lithography. Each semiconductor nanotrace 118, FIG. 1 inset, in the set of parallel nanotraces 115 provides a narrow electrical bridge between source 103 and drain 104 electrodes by making contact with the interdigitated finger region of each of the source 116 and drain 117 electroces. In the preferred embodiment (FIG. 1 inset), the dimensions of individual nanotraces 118 range between 10 nm to about 100 nm in width 119 and depth 120 where the depth 120 is defined by the thickness of the originally deposited semiconducting active layer. More preferable, the width of each nanotrace is less than about 50 nm. Most preferable, the width of each nanotrace is less than about 20 nm. Pitch 121 between neighboring nanotraces 118 in the set of parallel nanotraces 115 can vary depending on the number of nanotraces 118 included in the set and the total surface area of the interdigitated finger region of source 116 and drain 117 electrodes. The number of nanotraces 118 can range from one to hundreds depending on the application. The length 122 of the semiconductor nanotraces 118 spans the full distance from the outside source interdigitated finger 116 to the outside drain interdigitated finger 117 of each sensor device 102, crossing over all interdigitated fingers therebetween.

When an external electric field is applied across drain electrode 103 and source electrode 104, electrical current must travel through the set of parallel semiconductor nanotraces 115 to pass from the source electrode finger 116 to the drain electrode finger 117. Because the width 119 of each semiconductor nanotrace 118 is on the order of the electrical diffusion pathway and the surface-to-volume ratio for each nanotrace 118 is large, the current traveling through each nanotrace 118 is highly influenced by its local environment 123 near the surface. The response is proportional to the degree in which the electrical current traversing the set of semiconductor nanotraces 115 is influenced by changes in the electric field strength near the surface of each nanotrace 118. The local environment 123 can be a gas phase, e.g. an air plenum sampling for toxic gases, a solution environment e.g. and aqueous buffer sampling for complementary nucleic acids, or a solid environment e.g. an electrophoresis gel sampling for nucleotides on a nucleic acid sequence. The fabrication of a set of parallel nanotraces 115 serves to homogenize the total response to changes in local environment 123 since the total response is the average of the response of each nanotrace 118 connected in parallel between the interdigitated finger region of the source 116 and drain 117 electrodes. Averaging the response over a number of nanotraces 118 lowers the failure rate of sensor devices 102 during fabrication of the multiplex detection array 101. Because each nanotrace 118 is in direct electrical contact with the interdigitated finger region of source 116 and drain 117 electrode, contact resistance 124 between the two materials must be kept low. The present embodiment depicted in FIG. 1 shows a bottom contact approach for forming the electrical interface between semiconductor nanotrace 118 and the interdigitated finger region of source 116 and drain 117 electrodes, however, alternate methods which include top contact between the interdigitated finger region of source 116 and drain 117 electrodes can be used to make the electrodes. Because semiconductor nanotraces 118 are electrically continuous with the interdigitated finger region of the source 116 and drain 117 electrodes that work back to the source 109 and drain 114 electrode bonding pads through source 103 and drain electrode 104 and 104B, the source-to-drain current can be measured externally through electrodes that make contact with source 109 and drain 114 electrode bonding pads, Electrical continuity from the bonding pads to an electrode is established using common techniques such as wire or bump bonding of the multiplex detection array 101 chip to an electronics board package (not shown in FIG. 1).

Method for Patterning the Base Electrode Structures:

FIGS. 2A-F illustrate the series of fabrication steps for multiplex detection array 101 in preparation for binding of probe libraries specific to the type of test being performed. Initially, substrate 107 is used as a base for fabricating the array of sensor devices 102, FIG. 2A. Suitable materials for substrate 107 include any semiconductor or insulating wafer such as glass, doped or undoped semiconductors e.g. silicon, or polymers. Substrates such as flexible polymer films or metal foils may also be used. A series of parallel, individually-addressable gate electrodes 105 are deposited on substrate 107. If substrate 107 is semiconductor or electrically conducting, an insulating layer (not shown in FIG. 2) may be deposited prior to deposition of gate electrode 105 on substrate 107 to provide a means to prevent shorting of gate electrodes 105 to the substrate. A suitable material for gate electrodes 105 is a tie layer of chromium or titanium (~5 nm) and a gold electrode layer (~40-100 nm). A suitable means to deposit gate electrode layer 105 is vacuum deposition and a suitable means to subsequently pattern gate electrodes 105 is standard lithography. In the embodiment illustrated in FIG. 2A, each gate electrode 105 is common to an entire column of sensor devices that are subsequently deposited over gate electrode 105. Each gate electrode 105 terminates at a gate electrode bonding pad 108 that are positioned in an area remote from any sensor devices 102, depicted previously in FIG. 1, to enable facile connection with an external set of electrodes.

After patterning of gate electrodes 105, gate dielectric layer 106 is deposited by chemical vapor deposition. The thickness of the gate dielectric layer 106 is a balance between maximizing the field effect from gate electrode 105 and preventing electrical breakdown at too high of an electrical field. A suitable material for gate dielectric 106 is silicon dioxide and the thickness preferably ranges between 10 nm and 200 nm. The need for gate electrode 105 is dependent on the application of the multiplex detection array 101. As an alternative to that depicted in FIG. 2A, the gate electrode may be formed using standard ion implantation into substrate 107, which is well known in the art. Another embodiment might include using the entire substrate 107 as a common gate electrode. This does not require deposition and patterning of the metal gate electrode 105 although gate dielectric 106 is always deposited. Similarly, in another embodiment, the need for gate electrode 105 might be removed altogether as the chemiresistive measurement of sensor devices 102 may occur without preconditioning of the electrical properties of semiconductor nanotraces 118 using the field from a gate electrode 105.

The example illustrated in FIG. 2B shows common gate electrode 105 positioned below the column of sensor devices 102 created by sensor devices 102A and 102D in multiplex detection array 101. A continuous metallic layer is deposited over the surface of gate dielectric 106. The electrode material is composed of a tie layer (~5 nm of chromium or titanium) followed by a gold layer (~40-100 nm). The electrode materials may be deposited by thermal evaporation, electron beam evaporation, or some suitable other process. After deposition, a photolithography processing step is performed using a standard photoresist layer that is exposed and developed to generate the gold features that compose segments of both the source 103 and drain 104 electrodes. As part of the pattern, the interdigitated finger region for both source 116 and drain 117 electrodes are developed in a single layer with source electrode fingers 116 contiguous with the common source electrode 103. Source electrode 103 is also contiguous between the source side of each sensor device 102 for a given column. For example, the source electrode connects sensor devices 102A and 102D, 102B and 102E, and 102C and 102F in FIG. 2B. Each source electrode 103 terminates at a source electrode bonding pad 109. The source electrodes 103 are parallel with the gate electrodes 105 and terminate in an area remote from the sensor devices 102 in the multiplex detection array 101. The position of the source electrode bonding pads 109 is offset from the gate electrode bonding pads 108 to accommodate the necessary steps to liberate the gate dielectric 106 above the gate electrode bonding pads 108. Removal of a portion of the gate dielectric layer is illustrated as the gate electrode window 201 in FIG. 2B. Grouping of the source electrode bonding pads 109 in this region provides a means for facile electrode connectivity to an external electronic board (not shown).

The interdigitated fingers on the drain side 117 is contiguous with the first leg of drain electrode 104 which terminate with the drain electrode stub bonding pad 110 on each sensor device 102. The drain electrode stub bonding pad 110 serves as a termination point for subsequent transfer of the drain electrical connection into a secondary electrode plane (described later). In addition to the deposition of the electrode structures 103 and 104, alignment marks for aligning subsequent layers are also patterned into the gold electrode layer on the edges of multiplex detection array 101 that are not visible in FIG. 2.

Fabrication of the Semiconductor Nanotraces

After fabrication of the base electrode layers, a semiconducting active layer is deposited over the entire wafer. Chemical vapor deposition, electron beam deposition or other suitable methods may be employed. Suitable materials for the semiconducting active layer are Group IV, III-V, and II-VI materials including tin oxide ($SnO_2$), indium oxide ($In_2O_3$), and zinc oxide (ZnO) and other nitrides and chalcogenides. Using the method of nanoimprint lithography (NIL) and a series of dry etch processes, the semiconducting active layer is patterned into a set of parallel nanotraces 115 over the interdigitated finger region of the source 116 and drain 117 electrodes. A separate set of parallel nanotraces 115 are patterned over each sensor device 102, FIG. 2C. Each nanotrace 118 in the set of nanotraces 115 is patterned such that the long axis of the nanotrace 122 runs parallel with the column of sensor devices 102 and perpendicular with the interdigitated finger region of the source 116 and drain 117 of the source 103 and drain 104 electrodes.

Nanoimprint lithography is a special processing technique that enables nanodimension features to be patterned into the semiconducting active layer using a top down approach without the use of expensive stepper aligner tools. The dimensions of each semiconductor nanotrace 118 are critical for increasing the response sensitivity to a level that provides practical direct electrical transduction of target molecule binding. This is achieved because the surface-to-volume ratio of each semiconducting nanotrace 118 is large due to the small width 119 and depth 120 of the nanotrace 118 (FIG. 1 Inset). Using nanoimprint lithography, nanotraces can be patterned with physical geometries that are comparable to the grain dimensions of the nanotraces 118, making the molecular-semiconductor electronic interaction more pronounced. Nanodimension registration with the interdigitated finger regions of the source 116 and drain 117 is achieved using a nanoimprint processing tool such as Molecular Imprints Imprio 5500 (Austin, Tex.). Also noteworthy is that the distance between the gate electrode and the set of parallel nanotraces 115 is dictated by the thickness of layer 106 and is a known, regular distance for all of the nanotraces 118 in the set of parallel nanotraces 115. This is in contrast to nanowire sensors where the distance between the active semiconductor nanowire and the electric field from gate electrode 105 can lead to background inhomogeneities in the response. The details of the method of nanoimprint lithography are defined further in the following sections of this description.

Developing the Electrical Architecture for Addressing Each Drain Electrode

After fabrication of the set of parallel semiconducting nanotraces 115 over each sensor device 102, the remainder of the drain electrodes 104B is deposited, FIG. 2D-F. Before addition of the drain electrode layer, a photoresist layer is spun over the entire surface and patterned, FIG. 2D. The pattern includes "islands" of photoresist 202 that are designed to protect the set of parallel nanotraces 115. Source 109 and gate 108 electrode bonding pads are also protected during the remaining fabrication steps of multiplex detection array 101 (not shown in FIG. 2). Referring to FIG. 2D, an insulating oxide layer 111 (~50-100 nm) is first deposited over the entire wafer to insure that contiguous drain electrodes 104B are electrically isolated from the underlying layer and do not electrically short to source electrodes 103. Electrical continuity between drain electrode stub bonding pad 110 and the drain electrode layer 104E is created by first patterning a series of "vias" 112 through the oxide insulating layer 111 directly over each drain electrode stub bonding pad 110. Vias 112 are created using a dry etch process with a patterned photoresist layer as the etch stop. After complete etching of the oxide in the vias 112 is insured, a tie layer (~5 nm) and gold layer (~100-200 nm) are deposited over oxide insulating layer 111 to a thickness that insures complete filling of vias 112 and electrical continuity to the drain electrode continuity pad pickup 113 in the drain electrode layer 104B. Wet etching of the gold/tie layers lead to the formation of drain electrodes 104B that terminate at drain electrode bonding pads 114 in an area remote from the sensor devices 102. FIG. 2E shows the final drain electrode pattern. Drain electrodes 104B are perpendicular to source 103 and gate 105 electrodes in the underlying layer. Drain electrodes 104B provide electrical continuity between all sensor devices 102 in each row. FIG. 2E shows an example where a drain electrode 104B is electrically contiguous between sensor devices forming the row 102A, 102B, 102C and a second drain electrode 104B is contiguous across the row containing sensor devices 102D, 102E, 102F. Each of the drain electrodes terminates at a separate drain electrode bonding pad 114 which can be connected to an external electrical monitoring device.

Preparing the Final Device for Microfluidic Coupling

As a final measure, oxide protection layer 203 (~100 nm) is deposited over the entire surface of multiplex detection array 101 as illustrated in FIG. 2F. In order to recover the set of semiconductor nanotraces 115 over each sensor device 102 for further biomolecular or chemical coupling, final photoepoxy resist layer 204 is spin-coated and patterned over sensor devices 102 to provide a bonding face for a microfluidic cover plate. Photoepoxy resist layer 204 serves two purposes. First, photoepoxy resist layer 204 acts as the etch stop during the oxide dry etch which removes the oxide material back to protection islands 202 over the set of parallel nanotraces 115. After patterning of the photoepoxy resist, a dry etch process is used to remove the silicon dioxide from the final oxide protection layer 203 and the oxide layer 111 in that order. This produces access windows 205 to the semiconducting nanotraces 115 over each sensor device 102.

Photoepoxy resist layer 204 also serves as the final bonding and interface layer that makes contact to the microfluidic cover plate (described later). After the dry etch of the oxide layers is complete over protection islands 202, and protection islands 202 are stripped from the surface of the set of parallel semiconductor nanotraces 115, a light piranha etch (1 part 30% $H_2O_2$: 3 parts concentrated $H_2SO_4$) removes any residual organic residue from the surface of the set of semiconductor nanotraces 115 yielding a pristine semiconductor surface for covalent attachment of probe molecules. As a final measure, multiplex detection device 101 is treated with an oxygen ashing step 10-30 minutes at a pressure of 700 mTorr at a power of 300 W with $O_2$ flow of 8 sccm. Oxygen ashing leads to diffusion of $O^-$ into the bulk lattice of the semiconducting nanotrace 118 surface and completes the stoichiometric ratios necessary to convert the nanotraces 118 into a suitable material for molecule coupling and direct electrical transduction. Oxygen ashing is carried out using an instrument such as a March Asher and is preceded by a thermal annealing step (10 min. at 200° C.) in ambient.

Detailed Description of the Method of Nanoimprint Lithography

Fabrication of the set of parallel semiconductor nanotraces 115 is one of the core features of multiplex detection array 101. To fabricate the set of parallel nanotraces 115, the method of Nanoimprint Lithography (NIL) is employed. NIL was first described in the prior art by U.S. Pat. No. 6,334,960, which is hereby incorporated by reference herein. FIGS. 3A-E illustrate the process for preparing the nanoimprint features into the active semiconducting layer. The first step is to fabricate imprint template 301 that is a separate component to multiplex detection array 101. Template 301 is composed of a quartz wafer that has been previously patterned using electron beam lithography. The method for making the imprint template is described in the prior art by U.S. Pat. No. 6,334,960. Briefly, the electron beam writes individual features into an e-beam photoresist which after development appears as grooves in the resist. The pattern is transferred into a thin chromium layer ~30 nm thick using a dry etch process. The chromium layer is then used as a hard etch stop during a dry etch of the quartz wafer. The e-beam written features appear as "grooves" 302 in quartz template 301 with the desired pattern. The chromium layer is stripped leaving a transparent, nanopatterned quartz template 301 as a freestanding wafer. Quartz template 301 is shown above multiplex detection array 101 wafer in FIG. 3A. For reference, the fabrication step of multiplex detection array 101 captured in FIG. 3A is that previously illustrated in FIG. 2B. As a final measure, self-assembled "release" monolayer 303 is applied to the surface of template 301 by immersing template 301 into solution overnight followed by rinsing of excess. The fabrication of quartz template 301 is considered the "slow" step. Once fabricated, it can be used to make many copies of the nanoimprint pattern. FIGS. 3B-E show a cross-sectional view of the processing steps for preparing the set of parallel semiconductor nanotraces 115 using template 301. Template 301 is a full wafer which contains multiple copies of multiplex detection device 101, referred herein as the "die". The design of multiplex detection device 101 is created such that all of the sets of parallel nanotraces 115 for every sensor device 102 in a multiplex detection array 101, and all copies, or dies of the multiplex detection array 101 are fabricated during a single NIL process. However, FIGS. 3A-E illustrates a cross-sectional view of the NIL process sequence that occurs over only a single sensor device 102 in one of the multiplex detection device 101 dies.

Initially, quartz template 301 is positioned such that grooves 302 are registered over the interdigitated finger region of the sensor devices 102. As illustrated previously in FIG. 2C, the parallel set of semiconductor nanotraces 115 is perpendicular to interdigitated finger region of the source 116 and drain 117 portions of the electrodes spanning the distance therebetween. A hard mask or back anti-reflection coating (BARC) layer 304 (~60 nm) is deposited onto the device layer stack which, in this cross-section, consists of semiconductor active layer 305 (~20-100 nm) on gate dielectric 106 (~20-100 nm) which is on gate electrode 105 (~40 nm) and supported by substrate wafer 107 (~500 um). The cross-section view in FIGS. 3A-E represents a view that is parallel to interdigitated finger regions of the source 116 and drain 117 electrodes, but is in the space between adjacent source 116 and drain 117 fingers so they do not appear in this cross-sectional view.

After BARC layer 304 is spun cast onto the device stack, photoresist dispenser 306 places droplets of SFIL or other suitable nanoimprint photoresist 307 onto BARC layer 304 which spreads into a continuous thin layer 308 onto the surface. Referring to FIG. 3C, template 301 is brought into contact with photoresist 308. Template 301 is angled onto layer 304, so as to create a wave front of photoresist 308. This wave front expels gas pockets, resulting in complete filling of grooves 302 of template 301. Referring to FIG. 3D, ultraviolet light rays 309 (~300 W/cm$^2$, 20 s) expose photoresist 308 through template 301. Photoresist 308 reacts and polymerizes into rigid imprint layer 310. After exposure, template 301 is moved from the surface, leaving hard imprint layer 310 which have sharp imprint features 311 that are the negative of grooves 302 in template 301. The remaining area is a thin residual layer 312 between raised imprinted features 311. Template 301 is released from hard imprint layer 310 under the assistance of release layer 303 on template 301, FIG. 3E.

Figure 4A:
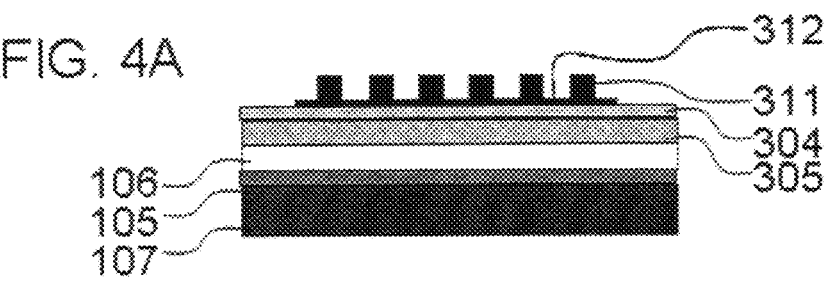
FIGS. 4 A-E illustrate the process for etching the semiconductor nanotraces.
Figure 4B:
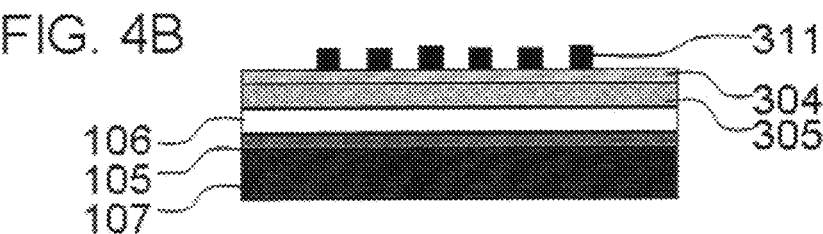
Figure 4C:
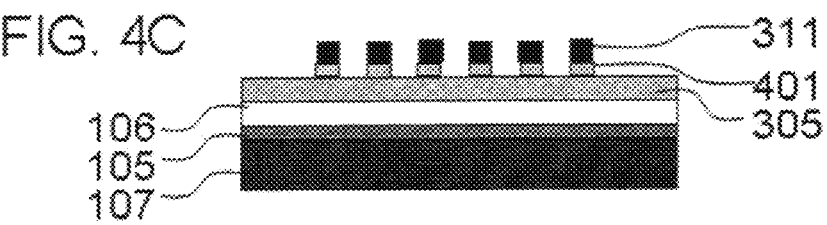

After hard imprint features 311 are formed, the features are "transferred" into semiconductor active layer 305 using a series of dry etch processes, FIGS. 4A-D. As a first step (FIG. 4A), a plasma dry etch system such as an Oxford Plasma Lab 80 RIE operating under a $CHF_3:O_2$ environment (15 sccm $CHF_3$, 7.5 sccm $O_2$, p=25 mTorr) and a DC bias of ~200 V was used to remove the residual silicon-containing SFIL polymer layer 312 at an etch rate of ~30-40 nm/min. (~50 s). A slight over-etch is used at this stage. This etch decreases the height of hard imprint features 311 while simultaneously removing residual layer 312. The net effect of this etch is to reveal the surface of the BARC (organic) layer 304. The next process is transfer of the pattern into the BARC layer using an organic dry etch of 100% $O_2$ (8 sccm, p=5 mTorr) and a DC bias of ~200 V at an etch rate of 20-30 nm/min. (~2 min. 15 s). The differential etch rate of the silicon-containing hard imprint layer 311 provides a means to selectively etch the BARC (organic) layer to the surface of semiconductor active layer 305. The BARC layer 304 is used to smooth out small surface roughness in the wafer and make the final etch into the semiconductor active layer 305 more uniform. The geometry of the etched BARC features 401 under the hard imprint layer 311 is shown in FIG. 4C.

Figure 4D:
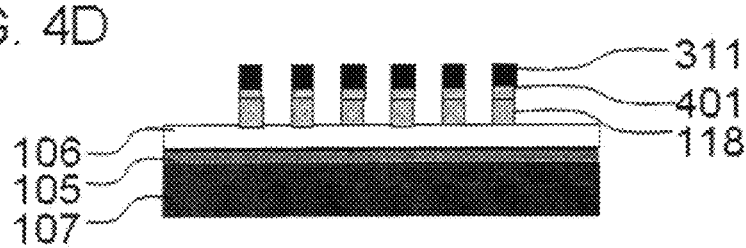
Figure 4E:
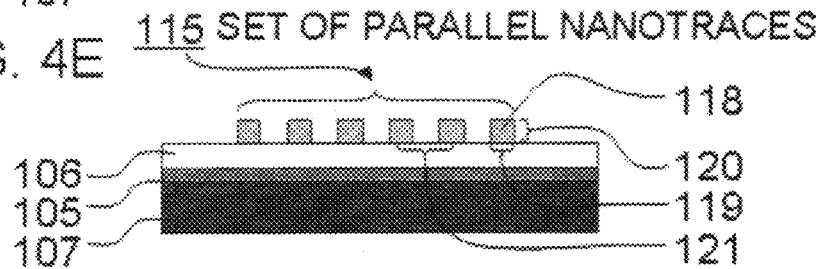

Referring to FIG. 4D, a final plasma etch step consisting of an $Ar:Cl_2$ gas mixture (24 sccm Ar, 6 sccm $Cl_2$, p=80 mTorr) at a bias of ~200 V, and an etch rate of 10-15 nm/min. (~1-3 mins. depending on the thickness of semiconductor active layer 305) is used to remove semiconductor active layer 305 and yield the set of parallel nanotraces 115. Each semiconductor nanotrace 118 has the width 119, depth 120, and spacing 121 defined previously in FIG. 2C. Alternatively, a hard mask layer, for example chromium, can be used if necessary to achieve the selectively and aspect ratio desired for semiconductor nanotraces 118. As a final step, FIG. 4E, etched hard imprint features 311 and etched BARC features 401 are removed using a piranha wet etch process. This process cleans the surface of semiconductor nanotraces 118 and prepares them for covalent attachment of probe molecules in later steps.

Figure 5:
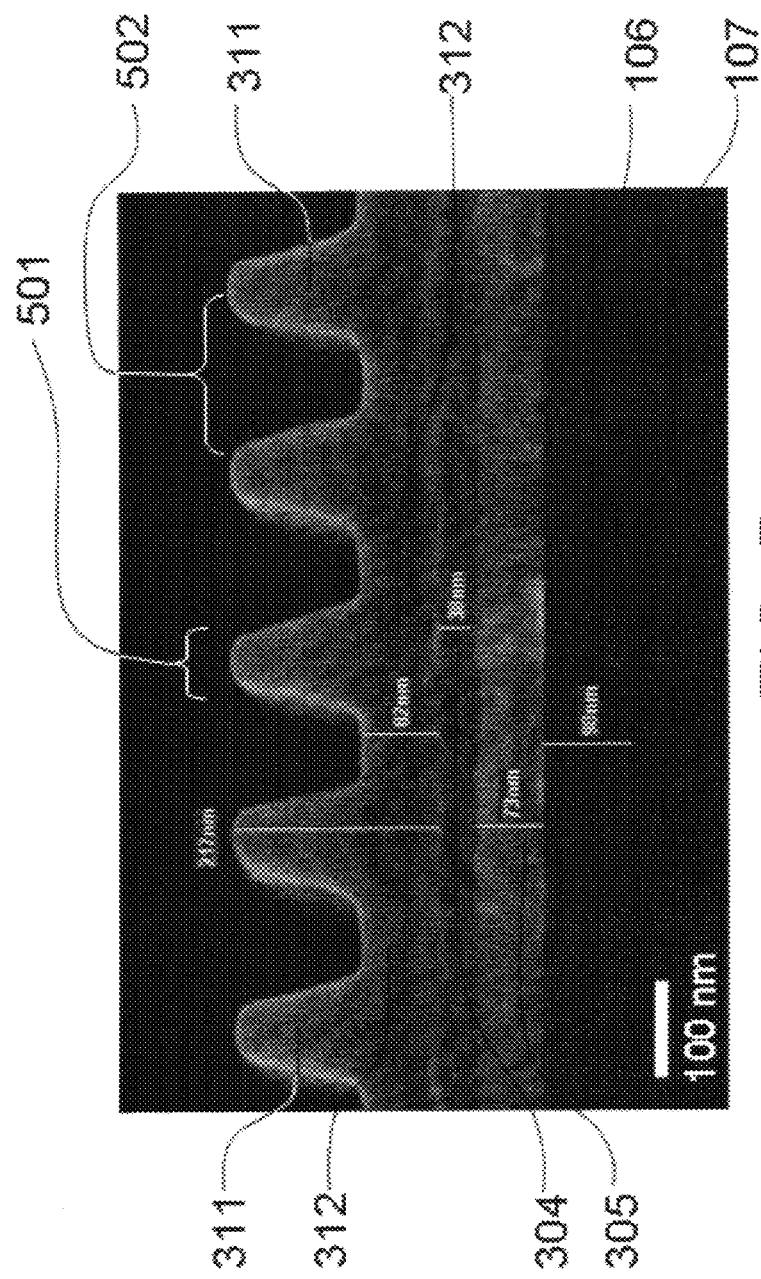
FIG. 5 shows a high resolution SEM of the imprinted SFIL over the semiconductor active layer.

FIG. 5 illustrates a High-Resolution Scanning Electron Microscope (HRSEM) cross-section micrograph of the process step just after nanoimprinting of the hard imprint features 311 over an example sensor device 102 (FIG. 1) in multiplex detection array 101. The photo micrographs are illustrative of the fabrication state depicted in FIG. 4A where base substrate 107, a p-doped silicon wafer (~500 μm) for example, is serving as gate electrode 105. A silicon dioxide layer (~100 nm) serves as gate dielectric 106 upon which the active semiconductor, $SnO_2$ layer 305 in this embodiment, is deposited (~70 nm). A back anti-reflection layer 304, Transpin™, is deposited on semiconductor active layer 305, upon which final SFIL layer 308 is deposited and patterned with the alternating regions of raised hard imprint features 311 (~150-300 in) and the thin residual layer 312 (~20-80 nm). Width 501 and spacing 502 of hard imprint features 311 are equal to the final desired width 119 and depth 120 of the individual semiconductor nanotraces 118.

Figures 6A, 6B:
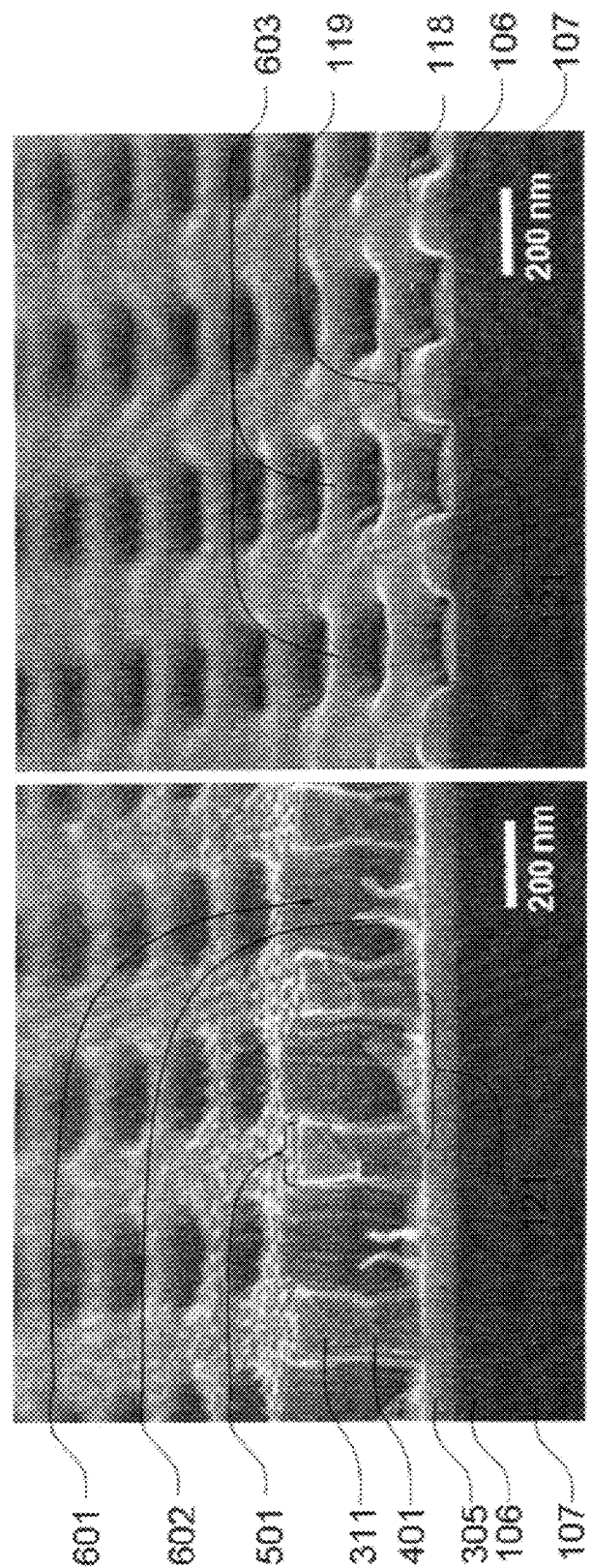
FIGS. 6 A-B show a high resolution SEM of the transfer of the imprint pattern to form the semiconductor nanotraces. This image depicts nanotraces with transverse bridging segments.

FIG. 6A illustrates a HRSEM photomicrograph after the breakthrough etch of the BARC layer 304 to semiconductor active layer 305 (example of etch state represented by FIG. 4C). Access of the reactant gases to the surface of semiconductor 305 is illustrated as 601 in the figure. Additionally, residual organic debris 602 can be seen and the best results occur when the dry etch of BARC layer 304 is carried out to completion to remove these features. FIG. 6B illustrates the process after completion of the dry etch of semiconductor active layer 305 and stripping of the etched BARC layer 304 and etched hard imprint layer 311 (example of state in FIG. 4E). The embodiment of semiconductor nanotraces 118 illustrated in FIG. 6B includes a semiconductor nanotraces design with bridging segments 603 between each semiconductor nanotrace 118 in the set of parallel semiconductor nanotraces 115. While the semiconductor nanotrace "mesh" embodiment is slightly altered from the previous illustration, ultimately the individual nanotraces 118 possess the same width 119 and spacing 120 of original hard imprint features 312. The pattern is simply altered by selection of a different design written into the template 301. After the process depicted in FIG. 6B is completed and the set of parallel nanotraces 115 are formed and cleaned free of organics, the multiplex detection array 101 is ready for deposition of the anchor probe library.

Synthesis of Anchor Probe Libraries on the Surface of the Active Semiconductor Nanotraces After fabrication of the electrical architecture of the multiplex detection device 101 illustrated previously in FIG. 2, the set of parallel semiconductor nanotraces 115 for each sensor device 102 is functionalized with a sensitizing compound. FIGS. 7A-C illustrate the steps for coupling the sensitizing compounds onto the surface of the parallel set of semiconductor nanotraces 115. Generally, each of the semiconductor nanotraces 118 within each parallel set of semiconductor nanotraces 115 receives the same sensitizing compound. In contrast, each parallel set of semiconductor nanotraces 115 on different sensor devices 102 receives a different sensitizing compound making it uniquely responsive to external targets relative to neighboring sensor devices 102 in the multiplex detection array 101. The collection of all the sensitizing compounds for a given multiplex detection device 101 is called the library. Different sensitization compounds from the library are added to each sensor device 102 by partitioning the sensor devices 102 into different reaction wells during coupling. Methods to segregate the different sensor devices 102 on multiplex detection device 101 during coupling of the sensitization compounds is described later.

Generally, the sensitizing compounds consist of "probe" molecules that are covalently attached to the surface of the semiconductor nanotraces 118. The probes have specific affinity for different targets. Methods that provide a means for parallel deposition of each anchored probe in the library onto the respective sets of parallel semiconductor nanotraces 115 and all of the sensor devices 102 in the multiplex detection array 101 during a single process is preferred. Generally, the specific anchored probes that are selected to be in the library of a given multiplex test are chosen based on known outcomes from individual sensor device and are representative of the type of test that is being performed. This simplest case consists of a single sensor device 102 that responds to a single or a plurality of specific targets.

In the preferred embodiment described in FIG. 7, the probe molecules in the compound library are nucleic acid sequences that are designed to respond very specifically to the binding of the complementary sequence. In other embodiments, the anchored probes could be proteins that respond differentially when the binding of different antibodies occur. Similarly, polymers or other macromolecules that exclude or specifically bind different solution analytes or gas phase analytes can be used as the sensitizing compound which makes the sensor device 102 unique. In the embodiment where the probe library consists of short nucleic acid sequences (oligonucleotides), individual oligonucleotides can be synthesized directly from the surface of the semiconductor nanotraces 118. A plurality of oligonucleotides can be synthesized onto the parallel set of semiconductor nanotraces on each sensor device using suitable methods such as PhotoGenerated Reagent (PGR) described in the prior art in U.S. Pat. No. 6,965,040, which is hereby incorporated by reference in its entirety. The method to deposit an anchor probe library of oligonucleotides using the method of PGR is illustrated in FIG. 7A-C and described below.

Initially, multiplex detection device 101, illustrated previously in FIG. 2F, is enclosed with microfluidic coverplate 701, FIG. 7A. Microfluidic plate 701 consists of a series of fluidic wells 702 (~15 um in depth) that are connected by a network of fluidic channels 703 (~90 um in depth) that work back to a single entrance and exit port (not shown) where fluidic coupling is made externally to a fluid manifold. The fluidic network consists of both parallel and serial connections of individual fluid wells 702 via fluidic network of channels 703. Microfluidic cover plate 701 can be glass or other suitable molded plastic component that provides a leak-tight seal between fluid wells 702. Additionally, the fluidic cover plate wafer must be transparent to support photoactivation of certain reagents during optical irradiation using the method of PGR. Each microfluidic well 702 is designed to fully enclose a single sensor device 102 in multiplex detection array 101. Each microfluidic well 702 provides a reaction center where photogenerated acid can diffuse throughout, but cannot cross into neighboring microfluidic wells 702. While synthesis of nucleic acid anchor probes is illustrated as the preferred embodiment in FIGS. 7A-C, other probe-specific classes such as proteins, small metabolites, nanoparticles, polymer nanospheres and other receptors for gas phases targets can also be deposited, or synthesized, depending on the application. Additionally, some of the sensor devices 102 in multiplex detection array 101 can be employed as references and controls. These sensor devices 102 would receive special sensitization compounds that may exclude, trap, or permit only a specific entity in the environment surrounding the semiconductor nanotraces 118. Likewise, sensor devices 102 may be designed to bind known sequences spiked into the sample solution, for example, as a positive control.

FIG. 7B illustrates the state of the multiplex detection array 101 after completion of the method of PGR. At this point, the microfluidic cover plate 702 is removed and the net result is a multiplex detection array 101 where the set of parallel nanotraces 115 on each sensor device 102 has a unique anchor probe molecule 704 synthesized on the surface of all of the semiconductor nanotraces 118 in the set of parallel nanotraces 115. FIG. 7B inset (i) illustrates that a plurality of copies of the same anchor probe oligonucleotide molecule 704 are synthesized from the surface of semiconductor nanotrace 118 and are limited only by the molecular packing density of the anchor probe molecules 704. At the end of the PGR process, the semiconductor nanotraces 118 for each sensor device 102 possess anchor probe molecules 704 covalently coupled to the surface where, in this example, the anchor probe sequence 705 is unique to a single sensor device 102. The unique anchor probe sequence 705, FIG. 7B(ii) for each sensor device 102 is dictated exclusively by the fluidic confinement of the PGR reagents within each microfluidic well 702 that enshroud the set of semiconductor nanotraces 115 on each sensor device 102. The number of different or redundant anchor probes 704 in the multiplex detection array 101 library is limited only by the number of sensor devices 102 and corresponding microfluidic wells 702 designed in the microfluidic cover plate 701.

As a final measure, multiplex detection array 101 with anchored probes 704 is packaged onto electronics board 706, FIG. 7C. Electrode bonding pads on multiplex detection device 101 are made contiguous with the electronics board 706 using a suitable technique such as wire or bump bonding. In the embodiment shown in FIG. 7C, a wire bond 707 connection is made between gate electrode bonding pad 108 and gate electronics control lead 708. Additionally, wire bond 709 between the source electrode bonding pad 109 and source electronics control lead 710, and wire bond 711 between the drain electrode bonding pad 114 and drain electronics control lead 712 are made. Some level of embedded logic is also included on the electronics board 706 (not shown) that enables multiplex signal acquisition, processing and results determination.

Detection of the Target Molecules

In the case of the preferred embodiment described above, the multiplex detection array 101 would be packaged within a common fluidic-tight vessel (not shown) that serves as the sample fluid reaction chamber which brings together the sample fluid with the multiplex detection array 101. For example, in the case of a diagnostic test for a virulent pathogen, the target nucleic acid sequence would bind with its complementary anchored probe oligonucleotide sequence 705 on one of the sensor devices 102 in the multiplex detection array 101. The sensor device 102 that bears the matching anchored probe oligonucleotide sequence 705 that is complementary to the target would incur a change in the source-drain electrical current which would be measured in the external circuit. A temperature controller device can be used to insure that the conditions for optimum binding affinity are achieved during reaction. A solid state cooler/heater device such as a thermoelectric cooler, for example, may be used in the instrument and pushed up against the cartridge when it is inserted into the instrument. Signal processing from the embedded control logic would then indicate to the user that the presence of the target nucleic acid sequence corresponding to a match with the known anchor probe sequence 705 was present in the sample. The result would be displayed on a digital display device that is part of the analysis instrument. The user would then determine a course of action based on the result of the diagnostic test. In the simplest case, a single sensor device 102 is used to determine the identity of an unknown target. The multiplex detection array 101 is designed to assess the presence of a single or plurality of targets during a single sample introduction onto multiplex detection array 101. The embedded control logic makes a continuous measurement of the current in all of the sensor, reference and control devices 102 in the multiplex detection array 101.

In alternate embodiments, the anchored probe oligonucleotide would be designed to look for a specific sequence that had been expressed such as RNA, or DNA that is specific to a particular organism. In other embodiments, the anchor probes may be nucleic acid sequences that have been selected based on a specific affinity to a target molecule or entity on a surface, e.g. a cell wherein the anchored probe sequence coils into a 3D conformation that interacts with the target in the form of an aptamer. In another embodiment, the anchor probe molecule may be a protein that has a specific affinity for a target protein or antigen, or the anchor probe molecule may be a small molecule that has a specific affinity for another molecule or ion in solution.

FIG. 8A-B illustrates the chemical binding effect of targets to the anchor probe molecules 704 on multiplex detection array 101. In this embodiment, anchor probes 704 synthesized on the surface of semiconductor nanotraces 118 display a baseline current 801 that is measured and recorded prior to introduction of target molecules 802, FIG. 8B. Upon addition of target molecule 802 to the fluid space above sensor device 102 (FIG. 8B), and if the target sequence 802 matches the anchor probe sequence 705 on any given sensor device 102 in the multiplex detection array 101, it will hybridize with the surface complement. Upon hybridization, the current traveling through the semiconductor nanotrace 118 will change at the point indicated by 803. Because anchor probe sequence 705 of sensor device 102 that undergoes a change in current is known, the identity of the unknown target sequence 802 can be made. The change in the current will be a new value 804 that indicates the presence of target 802. The magnitude and direction of the change in current is indicative of the concentration of target, nature of the surface interaction, local electric field and properties of the semiconductor nanotraces. The properties of the semiconductor nanotraces can be influenced by the doping level, external field applied by the gate electrode and other things that can affect or change the majority carrier concentration and mobility.

Although the present invention has been described with reference to specific details, it is not intended that such details should be regarded as limitations of the scope of the invention, except as and to the extent that they are included in the accompanying claims.

The invention claimed is:

1. A method for making an array of semiconductor nanotraces, comprising:
   (a) supplying a substrate;
   (b) forming a series of individually-addressable electrodes having bonding pads on the substrate using standard lithography;
   (c) depositing a layer of a semiconductor; and
   (d) using nanoimprint lithography (NIL) and dry etches to form a set of parallel nanotraces of the semiconductor between the electrodes.

2. The method of claim 1 further comprising depositing a dielectric layer before step (b).

3. The method of claim 2 further comprising depositing a gate electrode before depositing the dielectric layer such as to form a field effect transistor.

4. The method of claim 1 wherein the step of using NIL comprises:
   (a) applying a layer of organic material;
   (b) applying drops of polymerizable material;
   (c) contacting the polymerizable layer with a template having nanodimension depressions so as to cause the polymerizable material to flow into the depressions;
   (d) applying ultraviolet radiation to form polymerized material;
   (e) removing the template to leave raised features of the polymerized material that flowed into the depressions;
   (f) etching the polymerized and organic material;
   (g) etching the semiconductor; and
   (h) removing the remaining polymerized and organic material.

5. The method of claim 4 where the organic layer is a back anti-reflection coating.

6. The method of claim 4 wherein the organic layer is removed using a dry etch process with oxygen gas as the etchant.

7. The method of claim 4 wherein the polymerizable imprint layer is removed using a dry etch process with a mixture of a partially fluorinated hydrocarbon gas and oxygen.

8. The method of claim 4 where the semiconductor layer is removed using a dry etch process with a mixture of argon and chlorine.

9. The method of claim 4 where the polymerizable layer and the organic layer are stripped after transfer of the pattern into the semiconductor using a piranha wet etch.

10. The method of claim 1 wherein the substrate comprises doped silicon.

11. The method of claim 1 wherein the semiconductor layer is deposited using electron beam or vacuum evaporation.

12. The method of claim 1 wherein the semiconductor layer is deposited using molecular beam epitaxy, electron beam evaporation, or chemical vapor deposition.

13. The method of claim 1 wherein the semiconductor layer is deposited by spin casting.

14. The method of claim 1 wherein the semiconductor layer is deposited by sputter deposition.

15. The method of claim 1 wherein the semiconductor layer is annealed in different environments to condition the stoichiometry for the optimum electronic properties for sensing.

16. A method for making a multiplex array detection device, comprising:
   (a) supplying a substrate;
   (b) forming a series of individually-addressable electrodes having bonding pads on the substrate using standard lithography;
   (c) depositing a layer of semiconductor;
   (d) using nanoimprint lithography (NIL) and dry etches to form a set of parallel nanotraces of the semiconductor between the electrodes;
   (e) synthesizing selected anchor probe molecules on the semiconductor nanotraces; and
   (f) packaging the array onto an electronics board.

17. The method of claim 16 wherein the anchor probe molecules are synthesized by enclosing the semiconductor nanotraces in a microfluidic coverplate and using the method of Photo-Generated Reagent.

* * * * *